United States Patent [19]

Murakami et al.

[11] 4,454,323

[45] Jun. 12, 1984

[54] 1-METHYLTETRAZOL-5-YLTHIO ESTER OF CYANOMETHYLTHIOACETIC ACID

[75] Inventors: Masahiro Murakami; Masateru Kobayashi; Kimiyo Yamamoto, all of Nobeoaka; Chisei Shibuya, Fuji, all of Japan

[73] Assignee: Asahi Kasei Kogyo Kabushiki Kaisha, Tokyo, Japan

[21] Appl. No.: 545,202

[22] Filed: Oct. 25, 1983

Related U.S. Application Data

[63] Continuation of Ser. No. 298,884, Sep. 2, 1981.

[30] Foreign Application Priority Data

| Sep. 2, 1980 | [JP] | Japan | 55-120619 |
| Sep. 4, 1980 | [JP] | Japan | 55-121718 |
| Oct. 13, 1980 | [JP] | Japan | 55-142048 |
| Oct. 22, 1980 | [JP] | Japan | 55-146859 |
| Oct. 24, 1980 | [JP] | Japan | 55-148178 |
| Jul. 14, 1981 | [JP] | Japan | 56-108797 |

[51] Int. Cl.$^3$ .................................... C07D 257/04
[52] U.S. Cl. .................................................. 548/251
[58] Field of Search ........................................ 548/251

[56] References Cited

U.S. PATENT DOCUMENTS

| 3,946,003 | 3/1976 | Cooper | 424/246 |
| 4,144,391 | 3/1979 | Hatfield | 424/246 |
| 4,258,195 | 3/1981 | Shibuya et al. | 544/27 |
| 4,351,947 | 9/1982 | Shibuya et al. | 548/251 |

*Primary Examiner*—Paul M. Coughlan, Jr.
*Attorney, Agent, or Firm*—Finnegan, Henderson, Farabow, Garrett & Dunner

[57] ABSTRACT

Novel thioesters effective as acylating agents for amines or hydrazines, especially effective as active esters in synthesis of cephalosporin compounds are disclosed. The novel thioester of the present invention can be prepared by reacting a thiol or a derivative thereof with an acetic acid derivative or a reactive derivative thereof. By reacting the thioester of the present invention with a 7-aminocephalosporin derivative or a salt thereof, cephalosporin derivatives or pharmacologically acceptable salts thereof which are excellent antibiotic substances having a high antimicrobial activity can be obtained in high yield very safely.

1 Claim, No Drawings

1-METHYLTETRAZOL-5-YLTHIO ESTER OF CYANOMETHYLTHIOACETIC ACID

This is a continuation of application Ser. No. 298,884, filed Sept. 2, 1981.

The present invention relates to novel thioesters effective as acylating agents for amines and hydrazine especially effective as active esters in synthesis of cephalosporin compounds and a process for the preparation of the same, and a process for preparing cephalosporin derivatives and pharmacologically acceptable salts thereof by using the novel thioesters. More particularly the present invention is concerned with a novel thioester represented by the following general formula (I):

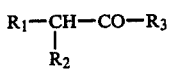

(I)

wherein $R_1$ stands for a p-hydroxyphenyl group, a trifluoromethylthio group, a cyanomethylthio group, a chlorine atom or a 2-thienyl group, $R_2$ stands for hydrogen atom or an amino or protected amino group, and $R_3$ stands for a 2-methyl-1,3,4-thiadiazol-5-ylthio group, a 1H-1,2,3-triazol-5-ylthio group or a 1-methyl-1,2,3,4-tetrazol-5-ylthio group, and a process for the preparation thereof which comprises reacting a thiol represented by the following general formula (II) or its derivative:

(II)

wherein $R_3$ is as defined above,
with an acetic acid derivative represented by the following general formula (III) or a reactive derivative thereof:

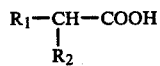

(III)

wherein $R_1$ and $R_2$ are as defined above,
and a process for the preparation of a cephalosporin derivative represented by the following general formula (V) or pharmacologically acceptable salts thereof:

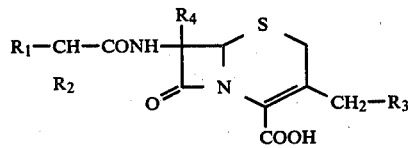

(V)

wherein $R_1$, $R_2$, and $R_3$ are as defined above, and $R_4$ stands for a hydrogen atom or a methoxy group, which comprises reacting a 7-aminocephalosporanic acid derivative represented by the following general formula (IV) or a salt thereof:

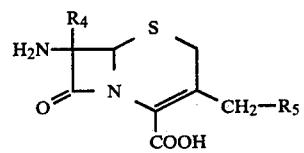

(IV)

wherein $R_4$ is as defined above, and $R_5$ stands for a halogen atom or an azido, acetoxy or benzimidazolylthio group,
with the above-mentioned novel thioesters (I).

Heretofore, cephalosporin derivatives represented by the general formula (V) have been prepared from 7-aminocephalosporinic acid or 7-methoxy-7-aminocephalosporanic acid through two steps. For example, there have been prepared cephalosporin derivatives represented by the general formula (V) according to a process in which 7-methoxy-7-(cyanomethylthioacetamido)cephalosporanic acid first produced by reacting 7-methoxy-7-aminocephalosporanic acid with cyanomethylthioacetic acid (see Japanese Patent Application Laid-Open Specification No. 65790/76) and this acid thus produced is then reacted with a 1-methyl-1,2,3,4-tetrazol-5-thiol to form a compound represented by the general formula (V) (see Japanese Patent Application Laid-Open Specification No. 65791/76), or a process in which 7-methoxy-7-amino-3-(1-methyl-1,2,3,4-tetrazol-5-ylthiomethyl)cephalosporanic acid is first produced by reacting 7-methoxy-7-aminocephalosporanic acid with 1-methyl-1,2,3,4-tetrazol-5-thiol (see Japanese Patent Publication No. 17936/64) and this acid thus produced is then reacted with cyanomethylthioacetic acid to form a compound represented by the general formula (V) (see Japanese Patent Application Laid-Open Specification No. 65790/76). Also, when 7-aminocephalosporanic acid is used as a starting material, cephalosporin derivatives represented by the general formula (V) have been prepared according to similar two-step processes to those as mentioned above.

Each of the two known processes comprises combination of two independent reactions, that is, acylation of the amino group at the 7-position of 7-aminocephalosporanic acid or 7-methoxy-7-aminocephalosporanic acid and substitution of the acetoxy group of the 3-acetoxymethyl group with a thio group of a thiol or vice versa. The two independent reactions are quite different from each other in reaction conditions, namely, the acylation reaction is carried out in a 50% aqueous solution of acetone at a temperature of 5° C. to room temperature while the substitution reaction is carried out in a 20 to 30% aqueous solution of acetone at 60° C. Therefore, even if it is intended to conduct the two reactions in a continuous manner, interruption of the reaction cannot be avoided for changing the reaction conditions. Moreover, these two reactions are carried out under severe conditions for cephalosporin compounds with respect to their stability, namely, at a pH value of 6.5 to 7.0 and at 5° C. to room temperature for 5 to 17 hours in the first stage of the two-stage process, and at a pH value of 6.5 to 7.5 and at 60° C. for 4 to 8 hours in the second stage. Such severe conditions affect the stability of cephalosporin compounds and hence lead to low yields. Therefore, such processes are not preferred from the economical viewpoint. In addition, if the reaction product obtained by practising the two-stage process in a continuous manner is purified, an adverse effect of the unreacted starting compounds and impurities such as compounds formed by decomposition upon the purity of the product cannot be neglected, so that it will be difficult to increase the purity of the product to a desired level. Moreover, methods heretofore used for acylation at the 7-position in the conventional processes, for example, the acid chloride method, the mixed acid anhydride method and the DCC condensation method, are remarkably defective in workability and safety because the acylating agents used in these methods decompose on contact with moisture and irritate human skin. As apparent from the foregoing, the conventional processes are not satisfactory from the commercial viewpoint.

In view of the current situation as mentioned above, the present inventors have made intensive investigations on chemical reactivities of the above-mentioned novel thioesters and the process for the preparation thereof. As a result of the investigations, the present inventors found that these thioesters are very effective and valuable as acylating agents for amines and hydrazines, for example, as active esters for the synthesis of cephalosporin compounds in which the amino group at the 7-position of 7-aminocephalosporin derivatives is acylated by the active ester and also found a process capable of preparing these thioesters very simply. Furthermore the present inventors found that these thioesters have such a reactivity that when they are reacted with 7-aminocephalosporin derivatives, two substituents can be introduced into the 7-aminocephalosporin derivatives to form cephalosporin derivatives represented by the above general formula (V) at a high efficiency without changing the reaction conditions or stopping the reaction in the midway. We have completed the present invention based on these findings.

In accordance with one aspect of the present invention, there is provided a novel thioester represented by the following general formula (I):

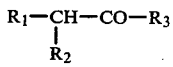
(I)

wherein $R_1$, $R_2$ and $R_3$ are as defined above.

In accordance with another aspect of the present invention, there is provided a process for the preparation of novel thioesters represented by the following general formula (I) which comprises reacting a thiol represented by the following general formula (II) or its derivative:

(II)

wherein $R_3$ is as defined above,
with an acetic acid derivative represented by the following general formula (III) or a reactive derivative thereof:

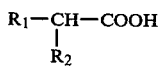
(III)

wherein $R_1$ and $R_2$ are as defined above.

In accordance with still another aspect of the present invention, there is provided a process for the preparation of a cephalosporin derivatives represented by the following general formula (V) or pharmacologically acceptable salts thereof:

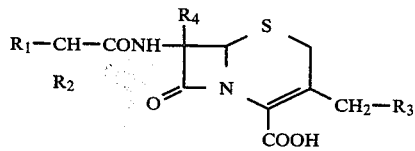
(V)

wherein $R_1$, $R_2$, $R_3$ and $R_4$ are as defined above, which comprises reacting a 7-aminocephalosporanic acid derivative represented by the following general formula (IV) or a salt thereof:

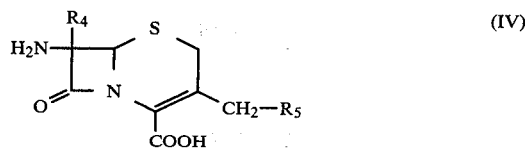
(IV)

wherein $R_4$ and $R_5$ are as defined above,
with a compound represented by the general formula (I).

The present invention will now be described in detail.

As the thioesters represented by the chemical formula (I), there can be mentioned a 2-methyl-1,3,4-thiadiazol-5-ylthio ester of p-hydroxyphenylglycine, a 1H-1,2,3-triazol-5-ylthio ester of p-hydroxyphenylglycine, a 1-methyl-1,2,3,4-tetrazol-5-ylthio ester of p-hydroxyphenylglycine, a 2-methyl-1,3,4-thiadiazol-5-ylthio ester of N-carbobenzyloxy-p-hydroxyphenylglycine, a 1H-1,2,3-triazol-5-ylthio ester of N-carbobenzyloxy-p-hydroxyphenylglycine, a 1-methyl-1,2,3,4-tetrazol-5-ylthio ester of N-carbobenzyloxy-p-hydroxyphenylglycine, a 2-methyl-1,3,4-thiadiazol-5-ylthio ester of N-formyl-p-hydroxyphenylglycine, a 1H-1,2,3-triazol-5-ylthio ester of N-formyl-p-hydroxyphenylglycine, a 1-methyl-1,2,3,4-tetrazol-5-ylthio ester of N-formyl-p-hydroxyphenylglycine, a 1-methyl-1,2,3,4-tetrazol-5-ylthio ester of trifluoromethylthioacetic acid, a 1-methyl-1,2,3,4-tetrazol-5-ylthio ester of cyanomethylthioacetic acid, a 1-methyl-1,2,3,4-tetrazol-5-ylthio ester of 2-thienylacetic acid and a 1-methyl-1,2,3,4-tetrazol-5-ylthio ester of chloroacetic acid.

These thioesters are novel substances which have not been introduced in any of literature references, and they are valuable as acylating agents for amines and hydrazines, for example, as important reactants in synthesis of medical cephalosporin derivatives.

In the thioester compound of the present invention represented by the general formula (I), since the thioester moiety

is very high in the reactivity, the thioester compound of the present invention can acylate easily amines or hydrazines, for example, an amino group at the 7-position of a 7-aminocephalosporin derivative in high yield. Furthermore, the thioester compound of the present invention can act as a reagent for effecting substitution at the 3-position in such 7-aminocephalosporin derivative.

More specifically, when 7-aminocephalosporanic acid is reacted with a 1H-1,2,3-triazol-5-ylthio ester of N-formyl-p-hydroxyphenylglycine, acylation of the amino group at the 7-position is easily advanced at a high yield, and surprisingly, the acetoxy group at the 3-position is simultaneously substituted with 1H-1,2,3-triazole-5-thiol, with the result that protection of the amino group is eliminated and 7-(p-hydroxyphenylglycinamido)-3-(1H-1,2,3-triazol-5-ylthiomethyl)-3-cephem-4-carboxylic acid (Cefatrizine), which is valuable as an antibiotic substance having a high microbial activity across abroad antimicrobial spectrum against various microorganisms inclusive of Gram-positive and Gram-negative pathogenic bacteria, can be easily obtained in a high yield.

Furthermore, when 7-methoxy-7-amino-3-(benzimidazolylthiomethyl)cephalosporanic acid is similarly reacted with, for example, a 1-methyl-1,2,3,4-tetrazol-5-ylthio ester of cyanomethylthioacetic acid, 7-methoxy-7-(cyanomethylthioacetamido)-3-(1-methyl-1,2,3,4-tetrazol-5-ylthiomethyl)-3-cephem-4-carboxylic acid (Cefmetazole) can be easily obtained in a high yield.

Various active esters capable of acylating 7-aminocephalosporanic acids are known. However, active esters capable of effecting acylation at a high conversion and simultaneously effecting substitution at the 3-position at a high conversion with ease, such as the thioester compounds of the present invention have not been known at all. Therefore, the thioesters of the present invention are epoch-making as active esters for the acylation of 7-aminocephalosporanic acids.

Even when the 7-aminocephalosporin derivative of the formula (IV) in which the group $R_5$ bonded to the methyl group of the 3-position is an acetoxy group, a halogen atom or an azido group, the reaction is sufficiently advanced in a neutral or weakly alkaline region, but if the group $R_5$ is a benzimidazolylthio group, this group is converted to an eliminated group having a very high reactivity in the presence of a proton and the substitution reaction is advanced very promptly in an acidic region where the cephalosporin compounds are stable. Accordingly, in this case, the reaction time can be shortened to 1/5, and the yield is about 1.5 times. As the substituent of the same series to be bonded to the methyl group of the 3-position, there can be mentioned benzthiazolylthio and benzoxazolylthio groups or the like. Even in case of such substituent, the reaction is advanced, but the benzimidazolylthio group is excellent in stability and reactivity.

The compounds of the following general formula (I) which are valuable and high in the reactivity as described above:

  (I)

wherein $R_1$, $R_2$ and $R_3$ are as defined above,
can easily be prepared in high yields by reacting a heterocyclic thiol represented by the following general formula (II) or its derivative:

$H-R_3$  (II)

wherein $R_3$ is as defined above,
with an acetic acid derivative represented by the following general formula (III) or a reactive derivative thereof:

  (III)

wherein $R_1$ and $R_2$ are as defined above.

In the case where $R_2$ of the acetic acid derivative of the general formula (III) is an amino group, the conversion is often highly improved by protecting this amino group by an appropriate protecting group. There can be used protecting groups customarily used, for example, formyl, carbobenzyloxy, carbo-t-butyloxy and ethyl acetoacetate groups. If the amino group is thus protected, the protected group is removed after completion of the reaction to obtain the intended compound.

As the derivative of the heterocyclic thiol of the general formula (II), there can be mentioned, for example, an alkali metal salt, a reaction product with a trialkyl aluminum, and a trialkylsilylated product.

As the reactive derivative of the acetic acid derivative represented by the general formula (III), there can be mentioned acid halides, acid anhydrides, mixed acid anhydrides, acid amides, esters and acid azides. As specific examples, there can be mentioned acid chlorides, alkyl carbonate mixed anhydrides and aliphatic carboxylic acid (for example, pivalic acid, pentanoic acid, isopentanoic acid, 2-ethylbutanoic acid, trichloroacetic acid and trifluoroacetic acid) mixed anhydrides. Equimolar amount of the compound of the general formula (III) to the amount of the compound of the general formula (II) is sufficient for carrying out the reaction successfully and the compound of the general formula (III) may be used in an amount ranging from 0.8 to 2.0 mols per mol of the compound of the general formula (II).

When free p-hydroxyphenylglycine, N-carbobenzyloxy-p-hydroxyphenylglycine or N-formyl-p-hydroxyphenylglycine is used as the reactant, a condensing agent is used for the reaction. As the condensing agent, there can be mentioned, for example, N,N'-dicyclohexylcarbodiimide, N,N'-diisopropylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N-ethyl-N'-(3-dimethylaminopropyl)carbodiimide and trifluoroacetic acid anhydride. In this case, equimolar amount of the compound of the general formula (III) to the amount of the compound of the general formula (II) is sufficient for carrying out the reaction successfully and the compound of the general formula (III) may be used in an amount ranging from 0.8 to 1.2 mols per mol of the compound of the general formula (II). The amount of the condensing agent of 0.5 mols or more per mol of the compound of the general formula (II) is sufficient for carrying out the reaction successfully. But it is preferred that the condensing agent be used in an amount of 0.8 to 1.5 mols per mol of the compound of the general formula (II) from the standpoint of efficiency, economy and post-treatment.

The reaction can be carried out at temperatures in the broad range of, for example, $-50°$ to $100°$ C., and the reaction may preferably be carried out at $-20°$ to $50°$ C.

The reaction may be carried out in a solvent. Any of solvents inert to the reactants and capable of dissolving or dispersing the reactants therein can be used. For example, there may be used ethers, esters, halogenated hydrocarbons and ketones. As specific examples, there can be mentioned dioxane, ethyl acetate, methylene chloride, chloroform and acetone.

The reaction time may be varied depending on the reaction temperature and the kind of the reactants to be used. Generally, 1 to 17 hours is preferred.

After completion of the reaction, the intended compound is isolated from the reaction mixture and purified according to customary procedures. For example, the intended compound can easily be recovered by removing the solvent by distillation, and washing and drying the residue.

A cephalosporin derivative represented by the general formula (V) or a pharmacologically acceptable salt thereof can easily be obtained as the final intended compound at a high efficiency by reacting the so obtained compound of the general formula (I) with a compound represented by the general formula (IV) in a solvent. It is sufficient if the amount of the compound of the general formula (I) is at least equimolar to the amount of the compound of the general formula (IV). It is, however, preferred from the economical viewpoint that the compound of the general formula (I) be used in an amount of 1.0 to 2.0 mols per mol of the compound of the general formula (IV). As the solvent, there can be mentioned, for example, amides such as N,N-dimethylformamide, N,N-diethylformamide, N,N-dimethylacetamide and N,N-diethylacetamide, alcohols such as methyl alcohol and ethyl alcohol, aliphatic ketones such as acetone and methylethyl ketone, ethers such as methyl cellosolve, halogenated hydrocarbons such as dichloromethane and chloroform, nitriles such as acetonitrile and propionitrile, and sulfoxides such as dimethylsulfoxide and diethylsulfoxide. These solvents may be used singly or in the form of a mixture of two or more of them or an aqueous mixture. From the viewpoints of the dissolving power and the conversion and also from the economical viewpoint, it is preferred acetone acetonitrile, methyl alcohol or an aqueous mixture thereof be used for 7-aminocephalosporanic acid and 7-methoxy-7-aminocephalosporanic acid, and N,N-dimethylformamide, N,N-dimethylacetamide or an aqueous mixture thereof be used for 7-amino-3-(benzimidazol-2-yl)thiomethyl-3-cephem-4-carboxylic acid and 7-methoxy-7-amino-3(benzimidazol-2-yl)thiomethyl-3-cephem-4-carboxylic acid.

As mentioned before, when a benzimidazolylthio compound, for example, 7-amino-3-(benzimidazol-2-yl)thiomethyl-3-cephem-4-carboxylic acid is used as the compound represented by the general formula (IV), the reaction is carried out in the presence of an acid catalyst. However, in the reaction system there is present not only a thiol compound formed from this compound but also a thiol compound formed by the substitution reaction, and therefore, an acid catalyst need not particularly be added. In order to shorten the reaction time and improve the conversion, however, it is preferred that an acid catalyst be added. As the acid catalyst, there can be mentioned mineral acids such as hydrochloric acid and sulfuric acid, and organic acid, for example, sulfonic acids such as p-toluenesulfonic acid, methanesulfonic acid, fatty acids such as propionic acid, and thiols such as 1-methyl-tetrazol-5-thiol. From the viewpoints of increase of the yield and shortening of the reaction time, mineral acids and thiols are especially preferred.

The acid catalyst is ordinarily added in an amount of 0.05 to 1 mol per mol of, for example, 7-amino-3-(benzimidazol-2-yl)thiomethyl-3-cephem-4-carboxylic acid.

When the group $R_5$ bonded to the methyl group at the 3-position of the general formula (IV) is an acetoxy group, a halogen atom or an azido group, an alkaline substance, for example, sodium bicarbonate is added in the reaction system so that the reaction is carried out in a neutral or weakly alkaline region (pH 7 to 8).

The reaction temperature may be varied according to the kind of the solvent, but ordinarily, the reaction is sufficiently advanced at a temperature of 10° to 100° C. From the viewpoints of the conversion and the stability of the cephalosporin skeleton, it is especially preferred that the reaction be carried at a temperature of 40° to 80° C.

The reaction time may be varied according to the kind of the group $R_5$ bonded to the methyl group at the 3-position of the general formula (IV) and the kind of the solvent, it is ordinarily sufficient if the reaction is conducted for 30 minutes to 10 hours. For example, when 7-amino-3-(benzimidazol-2-yl)thiomethyl-3-cephem-4-carboxylic acid is used and the reaction is carried out in water-containing N,N-dimethylformamide as the solvent at 60° C. in the presence of an acid catalyst, a reaction time of 30 minutes to 3 hours is sufficient. When acylation at the 7-position and substitution at the 7-position are conducted in a continuous manner according to the conventional process, 8 to 18 hours are necessary for completion of the reaction, and side reactions of the product with the reactants and decomposition of the product are caused. In view of this fact, it will readily be understood that the process of the present invention is very simple and economically advantageous.

In the present invention, the so obtained cephalosporin compound represented by the general formula (V) may be converted to a pharmacologically acceptable salt according to need. Namely, the cephalosporin compound can be converted to an alkali metal salt, an ammonium salt or an alkaline earth metal salt according to customary procedures. In preparing pharmaceuticals, these salts are especially advantageous because of their high water solubilities.

The thioester compound of the general formula (I) according to the present invention is a brownish yellow compound and has none of the moisture-absorbing property, irritating property and corrosive action. Accordingly, this thioester compound can easily be handled with safety, and the working environment and apparatus are not impaired by this compound at all, and high operation safety can be maintained assuredly. Accordingly, from the practical viewpoint, the compound of the present invention is excellent over the conventional compounds used for synthesis of cephalosporin compounds, and according to the present invention, cephalosporin compounds of the general formula (V), which are excellent antibiotic substances having a high antimicrobial activity, and pharmacologically acceptable salts thereof can be prepared in high yields very safely.

For the treatment of infection, the compounds produced by a process according to the present invention are preferably administered orally or parenterally, as is conventional for the administration of antibiotics; preferred formulations are tablets, capsules, injectible liquids and suspensions. The daily dosage of the compounds produced by a process according to the present invention will, naturally, vary depending upon the age, condition and body weight of the patient. However, the compounds will normally be administered in divided doeses of from about 250 mg to about 3,000 mg per day for adults, normally two or four times a day.

The present invention will now be described in detail with reference to the following Examples that by no means limit the scope of the invention.

EXAMPLE 1

In a 1-liter eggplant type flask equipped with a drying calcium chloride tube were charged 8.4 g of p-hydroxyphenylglycine, 6.6 g of 2-methyl-1,3,4-thiadiazol-5-thiol and 500 ml of ethyl acetate, and the mixture was stirred to form a solution. Then, 10.3 g of N,N'-dicyclohexylcarbodiimide was added to the solution and the mixture was stirred at 25° C. for 12 hours. The resulting reaction mixture was subjected to filtration to remove insoluble N,N'-dicyclohexylurea. The filtrate was distilled under reduced pressure and the obtained oily substance was dissolved in a small amount of ethyl acetate and then crystallized from a small amount of n-hexane. Filtration and drying were carried out according to customary procedures to obtain 6.2 g of a 2-methyl-1,3,4-thiadiazol-5-yl-thio ester of p-hydroxyphenylglycine in the form of brown crystals (the yield was 44%).

| | Elementary Analysis | |
|---|---|---|
| | Calculated | Found |
| C | 47.0% | 46.5% |
| H | 3.9% | 4.9% |
| N | 14.9% | 14.1% |
| C | 22.8% | 22.0% |

Mass Spectrum (m/e): M+ 281.

EXAMPLE 2

In a 2-liter eggplant type flask equipped with a drying calcium chloride tube were charged 30.1 g of p-hydroxy-N-carbobenzyloxyphenylglycine and 13.2 g of 2-methyl-1,3,4-thiadiazol-5-thiol and 1 liter of dry acetone, and the mixture was stirred to form a solution. Then 20.6 g of N,N'-dicyclohexylcarbodiimide was added to the solution and the mixture was stirred at 25° C. for 15 hours. The resulting reaction mixture was subjected to filtration to remove insoluble N,N'-dicyclohexylurea. The filtrate was distilled under reduced pressure and the obtained oily substance was subjected to removal of the carbobenzyloxy group with hydrobromic acid according to customary procedures. The product was extracted with ethyl acetate and the solvent was removed by distillation under reduced pressure, and the residue was recrystallized from acetone to obtain 12.9 g of a 2-methyl-1,3,4-thiadiazol-5-ylthio ester of p-hydroxyphenylglycine in the form of brown crystals (the yield was 45.9%).

EXAMPLE 3

Substantially the same procedures as in Example 2 were repeated except that 10.1 g of 1H-1,2,3-triazol-5-thiol was used instead of 2-methyl-1,3,4-thiadiazol-5-thiol, to obtain 11.9 g of a 1H-1,2,3-triazol-5-ylthio ester of p-hydroxyphenylglycine in the form of brown crystals (the yield was 47.6%).

| | Elementary Analysis | |
|---|---|---|
| | Calculated | Found |
| C | 48.0% | 47.2% |
| H | 4.0% | 5.1% |
| N | 22.4% | 21.9% |
| S | 12.8% | 12.2% |

Mass Spectrum (m/e): M+ 250.

EXAMPLE 4

Substantially the same procedure as in Example 1 were repeated except that 5.8 g of 1-methyltetrazol-5-thiol was used instead of 2-methyl-1,3,4-thiadiazol-5-thiol to obtain 6.9 g of a 1-methyltetrazol-5-thio ester of p-hydroxyphenylglycine in the form of brown crystals (the yield was 52.1%).

EXAMPLE 5

Substantially the same procedures as in Example 1 were repeated in the same manner except that 9.8 g of p-hydroxy-N-formylphenylglycine was used instead of p-hydroxyphenylglycine and a compound shown in Table 1 was used instead of 2-methyl-1,3,4-thiadiazol-5-thiol. The obtained results are shown in Tables 1 and 2.

TABLE 1

| | Starting Compound | Product | | |
|---|---|---|---|---|
| Run | Thiol | Amount (g) | Amount (g) | Yield (%) |
| a | 2-methyl-1,3,4-thiadiazol-5-thiol | 6.6 | 13.1 | 85 |
| b | 1H-1,2,3-triazol-5-thiol | 5.5 | 11.5 | 83 |
| c | 1-methyl-1,2,3,4-tetrazol-5-thiol | 5.8 | 12.7 | 87 |

TABLE 2

| | | Elementary Analysis (%) | | | | Mass Spectrum (m/e), |
|---|---|---|---|---|---|---|
| Run | Compound | C | H | N | S | M+ |
| a | 2-methyl-1,3,4-thiadiazol-5-thio ester of p-hydroxy-N—formylphenylglycine | 46.60 (calculated) 46.52 (found) | 3.56 3.73 | 13.59 13.53 | 20.71 20.61 | 309 |
| b | 1H—1,2,3-triazol-5-thio ester of p-hydroxy-N—formylphenylglycine | 47.48 (calculated) 47.42 (found) | 3.60 3.66 | 20.14 20.00 | 11.51 11.29 | 278 |
| c | 1,2,3,4-tetrazol-5-thio ester of p-hydroxy-N—formylphenylglycine | 45.05 (calculated) 44.96 (found) | 3.75 3.92 | 23.89 23.66 | 10.92 10.67 | 293 |

EXAMPLE 6

A 1-liter eggplant type flask equipped with a drying calcium chloride tube was charged with 8.4 g of p-hydroxyphenylglycine and 5.1 g of 1H-1,2,3-triazol-5-thiol, and 400 ml of dry acetone was added and the mixture was stirred to form a solution. Then, 10.3 g of N,N'-dicyclohexylcarbodiimide was added and the mixture was stirred at 25° C. for 6 hours. The resulting reaction mixture was subjected to filtration to remove insoluble N,N'-dicyclohexylurea. The filtrate was distilled under reduced pressure and the obtained oily substance was dissolved in a small amount of ethyl acetate and then crystallized from a small amount of n-hexane. Filtration and drying are carried out according to customary procedures to obtain 5.3 g of a 1H-1,2,3-triazol-5-ylthio ester of p-hydroxyphenylglycine (the yield was 43%).

| | Elementary Analysis | |
|---|---|---|
| | Calculated | Found |
| C | 48.00 | 47.12 |
| H | 4.00 | 4.69 |
| N | 22.40 | 21.93 |
| S | 12.80 | 12.61 |

Mass Spectrum (m/e): M+ 250.

EXAMPLE 7

Substantially the same procedures as in Example 2 were repeated except that 11.6 g of 1-methyl-1,2,3,4-tetrazol-5-thiol was used instead of 2-methyl-1,3,4-thiadiazol-5-thiol, to obtain 11.5 g of a 1-methyl-1,2,3,4-tetrazol-5-ylthio ester of p-hydroxyphenylglycine in the form of a brown solid (the yield was 43.4%).

EXAMPLE 8

A 2-liter eggplant type flask equipped with a drying calcium chloride tube was charged with 30.1 g of p-hydroxyphenyl-N-carbobenzyloxyglycine and 13.2 g of 2-methyl-1,3,4-thiadiazol-5-thiol, and 1 liter of dry acetone was added and the mixture was stirred to form a solution. Then, 20.6 g of N,N'-dicyclohexylcarbodiimide was added to the solution and the mixture was stirred at 25° C. for 20 hours. The resulting reaction mixture was subjected to filtration to remove insoluble N,N'-dicyclohexylurea. The solvent was removed from the filtrate by distillation under reduced pressure and the residue was dissolved in dry ethyl acetate. A small amount of n-hexane was added to the solution to effect crystallization, and the crystallization product was dried to obtain 31.54 g of a 2-methyl-1,3,4-thiadiazol-5-ylthio ester of N-carbobenzyloxy-p-hydroxyphenylglycine in the form of a brown solid (the yield was 76%).

| | Elementary Analysis | |
|---|---|---|
| | Calculated | Found |
| C | 54.94% | 54.66% |
| H | 4.10% | 4.21% |
| N | 10.12% | 10.06% |
| S | 15.42% | 15.33% |

Mass Spectrum (m/e): M+ 415.

EXAMPLE 9

Substantially the same procedures as in Example 8 were repeated except that a thiol shown in Table 3 was used instead of 2-methyl-1,3,4-thiadiazol-5-thiol. The obtained results are shown in Tables 3 and 4.

TABLE 3

| | Starting Compound | Product | | |
|---|---|---|---|---|
| Run | Thiol | Amount (g) | Amount (g) | Yield (%) |
| a | 1H-1,2,3-triazol-5-thiol | 10.1 | 28.4 | 74 |
| b | 1-methyl-1,2,3,4-tetrazol-5-thiol | 11.6 | 27.1 | 68 |

TABLE 4

| Run | Compound | Elementary Analysis (%) | | | | Mass Spectrum (m/e) M+ |
|---|---|---|---|---|---|---|
| | | C | H | N | S | |
| a | 1H-1,2,3-triazol-5-ylthio ester of N—carbobenzyloxy-p-hydroxyphenylglycine | 56.25 (calculated) 56.01 (found) | 4.17 4.52 | 14.58 14.11 | 8.33 8.07 | 384 |
| b | 1-methyl-1,2,3,4-tetrazol-5-ylthio ester of N—carbobenzyloxy-p-hydroxyphenylglycine | 54.14 (calculated) 53.98 (found) | 4.26 4.53 | 17.54 17.49 | 8.02 7.92 | 399 |

EXAMPLE 10

A 1-liter eggplant type flask equipped with a drying calcium chloride tube was charged with 16.0 g of trifluoromethylthioacetic acid and 11.6 g of 1-methyl-tetrazol-5-thiol, and 500 ml of dry ethyl acetate was added and the mixture was stirred to form a solution. Then, 20.6 g of N,N'-dicyclohexylcarbodiimide was added to the solution and the mixture was stirred at 25° C. for 12 hours. The resulting reaction mixture was subjected to filtration to remove insoluble N,N'-dicyclohexylurea. The filtrate was distilled under reduced pressure, and the obtained oily substance was dissolved in a small amount of ethyl acetate and then crystallized from a small amount of n-hexane. Filtration and drying were carried out according to customary procedures to obtain 20.8 g of a 1-methyltetrazol-5-ylthio ester of trifluoromethylthioacetic acid in the form of dark brown crystals (the yield was 81%).

| | Elementary Analysis | |
|---|---|---|
| | Calculated | Found |
| C | 23.3% | 23.2% |
| N | 21.7% | 21.9% |
| S | 24.8% | 24.7% |
| F | 22.1% | 22.1% |
| H | 1.9% | 1.9% |

Mass Spectrum (m/e): M+258.

EXAMPLE 11

A 300-ml eggplant type flask equipped with a drying calcium chloride tube was charged with 3.2 g of trifluoromethylthioacetic acid and 1.35 g of 1-methyltetrazol-5-thiol, and 200 ml of dry acetone was added and the mixture was stirred to form a solution. Then, 4.12 g of N,N'-dicyclohexylcarbodiimide was added to the solution and the mixture was stirred at 25° C. for 15 hours. The resulting reaction mixture was subjected to filtration to remove insoluble N,N'-dicyclohexylurea. The filtrate was distilled under reduced pressure and the obtained oily substance was dissolved in a small amount of ethyl acetate, and the solution was allowed to stand in a refrigerator for 15 hours to form crystals. The crystals was recovered by filtration and dried according to customary procedures to obtain 3.92 g of a 1-methyltetrazol-5-ylthio ester of trifluoromethylthioacetic acid in the form of dark brown crystals (the yield was 76).

EXAMPLE 2

A 500 ml eggplant type flask equipped with a drying calcium chloride tube was charged with 6.55 g of cyanomethylthioacetic acid and 5.8 g of 1-methyltetrazol-5-thiol, and 300 ml of dry ethyl acetate was added and the mixture was stirred to form a solution. Then, 10.3 g of N,N'-dicyclohexylcarbodiimide was added to the solution, and the mixture was stirred at 25° C. for 14 hours. The resulting reaction mixture was subjected to filtration to remove insoluble N,N'-dicyclohexylurea. The filtrate was distilled under reduced pressure, and the obtained oily substance was dissolved in a small amount of ethyl acetate and then crystallized from a small amount of n-hexane. The crystals were recovered by filtration and dried according to customary procedures to obtain 9.5 g of a 1-methyltetrazol-5-ylthio ester of cyanomethylthioacetic acid in the form of dark yellow crystals (the yield was 83%).

| Elementary Analysis | | |
|---|---|---|
| | Calculated | Found |
| C | 31.4% | 31.2% |
| N | 30.6% | 30.7% |
| S | 27.9% | 27.7% |
| H | 3.1% | 3.3% |

Mass Spectrum (m/e): M+ 229.

EXAMPLE 13

A 1-liter eggplant type flask equipped with a drying calcium chloride tube was charged with 13.1 g of cyanomethylthioacetic acid and 11.6 g of 1-methyltetrazol-5-thiol, and 600 ml of dry acetone was added and the mixture was stirred to form a solution. Then, 20.6 g of N,N'-dicyclohexylcarbodiimide was added to the solution and the mixture was stirred at 25° C. for 15 hours. The resulting reaction mixture was subjected to filtration to remove insoluble N,N'-dicyclohexylurea. The filtrate was distilled under reduced pressure, and the obtained oily substance was dissolved in a small amount of ethyl acetate and then crystallized from a small amount of n-hexane. The crystals were recovered by filtration and dried according to customary procedures to obtain 19.5 g of a 1-methyltetrazol-5-ylthio ester of cyanomethylthioacetic acid in the form of dark yellow crystals (the yield was 85%).

EXAMPLE 14

A 1-liter eggplant type flask equipped with a drying calcium chloride tube was charged with 14.2 g of 2-thienylacetic acid and 11.6 g of 1-methyltetrazol-5-thiol, and 700 ml of dry ethyl acetate was added and the mixture was stirred to form a solution. Then, 20.6 g of N,N'-dicyclohexylcarbodiimide was added to the solution and the mixture was stirred at 25° C. for 12 hours. The resulting reaction mixture was subjected to filtration to remove insoluble N,N'-dicyclohexylurea. The filtrate was distilled under reduced pressure, and the obtained oily substance was dissolved in a small amount of ethyl acetate and then crystallized from a small amount of n-hexane. The crystals were recovered by filtration and dried according to customary procedures to obtain 19.0 g of a 1-methyltetrazol-5-ylthio ester of 2-thienylacetic acid in the form of brown crystals (the yield was 79%).

| Elementary Analysis | | |
|---|---|---|
| | Calculated | Found |
| C | 40.0% | 40.1% |
| N | 23.3% | 23.2% |
| S | 26.7% | 26.8% |
| H | 3.3% | 3.3% |

Mass Spectrum (m/e): M+ 240.

EXAMPLE 15

A 2-liter eggplant type flask equipped with a drying calcium chloride tube was charged with 18.9 g of 2-chloroacetic acid and 23.2 g of 1-methyltetrazol-5-thiol, and 1 liter of dry acetone was added and the mixture was stirred to form a solution. Then, 41.2 g of N,N'-dicyclohexylcarbodiimide was added to the solution and the mixture was stirred at 25° C. for 12 hours. The resulting reaction mixture was subjected to filtration to remove insoluble N,N'-dicyclohexylurea. The filtrate was distilled under reduced pressure, and the obtained oily substance was dissolved in a small amount of ethyl acetate and then crystallized from a small amount of n-hexane. The crystals were recovered by filtration and dried according to customary procedures to obtain 30.8 g of a 1-methyltetrazol-5-ylthio ester of 2-chloroacetic acid in the form of brown crystals.

| Elementary Analysis | | |
|---|---|---|
| | Calculated | Found |
| C | 35.60% | 35.52% |
| H | 3.21% | 3.43% |
| N | 20.77% | 20.71% |
| S | 15.82% | 15.77% |
| Cl | 8.78% | 8.76% |

Mass Spectrum (m/e): $M^{+2}$ 194.

EXAMPLE 16

2.7 g of 7-aminocephalosporanic acid was charged into a 300 ml three-necked flask and then dissolved in 100 ml of an aqueous solution of sodium hydrogencarbonate so that the resulting solution had a pH value of 7.0 to 7.5. A solution of 3.0 g of a 2-methyl-1,3,4-thiadiazol-5-ylthio ester of p-hydroxyphenylglycine in 50 ml of acetone was dropped into the three-necked flask over a period of 15 minutes at room temperature. The resulting mixture was heated at 60° C. and stirred for 7 hours while adding sodium hydrogencarbonate so that the pH value of the liquid was maintained at 6.8. After completion of the reaction, the acetone was removed by distillation under reduced pressure and the resulting concentrate was subjected to fractional high-speed liquid chromatography to obtain a fraction of the intended product. The fraction was concentrated under reduced pressure to obtain 29 g of 7-(p-hydroxyphenyl-glycinamido)-3-(2-methyl-1,3,4-thiadiazol-5-yl)thiomethylcephalosporanic acid in the form of a yellow powder (the yield was 60%). The product had a purity of 80%.

Conditions for Fractional High-Speed Liquid Chromatography

Chromatograph: System Model 500 supplied by Waters Assoc. Co.
Solvent: methanol/water (40/60 by volume)
Column: fractional column, Prep-PAK C18
Flow rate: 100 ml/min

EXAMPLE 17

3.6 g of 7-amino-3-(benzimidazol-2-yl)thiomethylcephalosporanic acid was charged into a 500-ml three-necked flask and then dissolved in 100 ml of an aqueous solution of sodium hydrogencarbonate so that the resulting solution had a pH value of 7.0 to 7.5. A solution of 2.7 g of a 1H-1,2,3-triazol-5-ylthio ester of p-hydroxyphenylglycine in 50 ml of dimethylformamide was dropped into the three-necked flask over a period of 15 minutes at room temperature. The pH value of the resulting mixture was adjusted to 4.1 by diluted hydrochloric acid, and the mixture was heated at 60° C. and stirred for 2 hours. After completion of the reaction, the resulting reaction mixture was subjected to fractional high-speed liquid chromatography to obtain a fraction of the intended product. The fraction was concentrated under reduced pressure and freeze-dried to obtain 3.7 g of 7-(p-hydroxyphenylglycinamido)-3-(1H-1,2,3- triazol-5-yl)thiomethylcephalosporanic acid in the form of a white solid (the yield was 81%). The product had a purity of 91%.

Conditions for Fractional High-Speed Liquid Chromatography

Chromatograph: System Model 500 supplied by Waters Assoc. Co.
Solvent: methanol/water (40/60 by volume)
Column: fractional column Prep-PAK C18
Flow rate: 100 ml/min

EXAMPLE 18

3.6 g of 7-amino-3-(benzimidazol-2-yl)thiomethyl-cephalosporanic acid was charged into a 300-ml three-necked flask and then dissolved in 100 ml of an aqueous solution of sodium hydrogencarbonate so that the resulting solution had a pH value of 7.0 to 7.5. A solution of 3.0 g of a 1H-1,2,3-triazol-5-ylthio ester of p-hydroxy-N-formylphenylglycine in 50 ml of dimethylformamide was dropped into the three-necked flask over a period of 15 minutes at room temperature. The pH value of the liquid mixture was adjusted to 4.1 by diluted hydrochloric acid, and the mixture was heated at 60° C. and stirred for 1 hour. Then, the pH value of the resulting reaction mixture was adjusted to 8.0 by sodium hydrogencarbonate to effect deformylation. After completion of the deformylation, the liquid reaction mixture was directly subjected to fractional high-speed liquid chromatography to obtain a fraction of the intended product. The fraction was concentrated under reduced pressure and freeze-dried to obtain 3.7 g of 7-(p-hydroxyphenylglycinamido)-3-(1H-1,2,3-triazol-5-yl)thiomethylcephalosporanic acid in the form of a white solid (the yield was 85%). The product had a purity of 93%.

Conditions for the fractional high-speed liquid chromatography were the same as those adopted in Example 17.

EXAMPLE 19

Substantially the same procedures as in Example 18 were repeated except that a compound shown in Table 5 was used instead of the 1H-1,2,3-triazol-5-ylthio ester of p-hydroxy-N-formylphenylglycine. The obtained results are shown in Table 5.

EXAMPLE 20

3.6 g of 7-amino-3-(benzimidazol-2-yl)thiomethyl-cephalosporanic acid was charged into a 300-ml three-necked flask, and then dissolved in 100 ml of an aqueous solution of sodium hydrogencarbonate so that the resulting solution had a pH value of 7.0 to 7.5. A solution of 4.0 g of a 1H-1,2,3-triazol-5-ylthio ester of N-carbobenzyloxy-p-hydroxyphenylglycine in 50 ml of dimethylformamide was dropped into the three-necked flask over a period of 15 minutes at room temperature. The pH value of the liquid mixture was adjusted to 4.1 by diluted hydrochloric acid, and the mixture was heated at 60° C. and stirred for 1.5 hours. After completion of the reaction, the pH value of the resulting reaction mixture was adjusted to 2.0 by hydrochloric acid and the reaction mixture was extracted with ethyl acetate. The ethyl acetate was removed from the extract by distillation under reduced pressure and the residue was dissolved in an aqueous solution of hydrobromic acid and the solution was stirred at room temperature for 5 hours. After completion of the reaction, the resulting reaction mixture was subjected to fractional high-speed liquid chromatography to obtain a fraction of the intended product. The fraction was concentrated under reduced pressure and freeze-dried to obtain 3.9 g of 7-(p-hydroxyphenylglycinamido)-3-(1H-1,2,3-triazol-5-yl)thiomethylcephalosporanic acid in the form of a white solid (the yield was 85%). The product had a purity of 93%.

Conditions for Fractional High-Speed Liquid Chromatography

Chromatograph: System Model 500 supplied by Waters Assoc. Co.
Solvent: methanol/water (40/60 by volume)
Column: fractional column, Prep-PAK C18
Flow rate: 100 ml/min

EXAMPLE 21

3.0 g of 7-methoxy-7-aminocephalosporanic acid was charged into a 300-ml three-necked flask, and then dissolved in 100 ml of an aqueous solution of sodium hydrogencarbonate so that the resulting solution had a pH value of 7.0 to 7.5. A solution of 3.0 g of a 2-methyl-1,3,4-thiadiazol-5-ylthio ester of p-hydroxyphenylglycine in 50 ml of acetone was dropped into the three-necked flask over a period of 15 minutes at room temperature. The liquid mixture was heated at 60° C. and

TABLE 5

| | Starting Compound | | Product | | | |
|---|---|---|---|---|---|---|
| Run | Kind | Amount (g) | Kind | Amount (g) | Yield (%) | Purity (%) |
| a | 2-methyl-1,3,4-thiadiazol-5-ylthio ester of p-hydroxy-N—formylphenylglycine | 3.3 | 7-(p-hydroxyphenylglycyl)-amido-3-(2-methyl-1,3,4-thiadiazol-5-yl)thiomethylcephalosporanic acid | 4.3 | 87 | 95 |
| b | 1-methyl-1,2,3,4-tetrazol-5-ylthio ester of p-hydroxy-N—formylphenylglycine | 3.2 | 7-(p-hydroxyphenylglycyl)-amido-3-(1-methyl-1,2,3,4-tetrazol-5-yl)thiomethylcephalosporanic acid | 4.0 | 83 | 92 | stirred for 7 hours while adding sodium hydrogencarbonate so that the pH value of the liquid mixture was maintained at 6.8. After completion of the reaction, the acetone was removed by distillation under reduced pressure and the residue was subjected to fractional high-speed liquid chromatography to obtain a fraction of the intended product. The fraction was concentrated under reduced pressure to obtain 2.7 g of 7-(p-hydroxyphenylglycinamideo)-7-methoxy-3-(2-methyl-1,2,4-thiadiazol-5-yl)thiomethylcephalosporanic acid in the form of a yellow powder (the yield was 52%). The product had a purity of 80%.

Conditions for Fractional High-Speed Liquid Chromatography

Chromatograph: System Model 500 supplied by Waters Assoc. Co.
Solvent: methanol/wafter (40/60 by volume)
Column: fractional column, Prep-PAK C18
Flow rate: 100 ml/min

EXAMPLE 22

3.9 g of 7-methoxy-7-amino-3-(benzimidazol-2-yl)thiomethylcephalosporanic acid was charged into a 300-ml three-necked flask, and then dissolved in 100 ml of an aqueous solution of sodium hydrogencarbonate so that the resulting solution had a pH value of 7.0 to 7.5. A solution of 2.7 g of a 1H-1,2,3-triazol-5-ylthiol ester of p-hydroxyphenylglycine in 50 ml of dimethylformamide was dropped into the three-necked flask over a period of 15 minutes at room temperature. The pH value of the liquid mixture was adjusted to 4.1 by diluted hydrochloric acid, and the mixture was heated at 60° C. and stirred for 1 hour. After completion of the reaction, the liquid reaction mixture was subjected to fractional high-speed liquid chromatography to obtain a fraction of the intended product, and the fraction was concentrated under reduced pressure and freeze-dried to obtain 3.1 g of 7-(p-hydroxyphenylglycinamido)-7-methoxy-3-(1H-1,2,3-triazol-5-yl)thiomethylcephalosporanic acid in the form of a white solid (the yield was 61%). The product had a purity of 91%.

Conditions for Fractional High-Speed Liquid Chromatography

Chromatograph: System Model 500 supplied by Waters Assoc. Co.
Solvent: methanol/water (40/60 by volume)
Column: fractional column, Prep-PAK C18
Flow rate: 100 ml/min

EXAMPLE 23

3.9 g of 7-methoxy-7-amino-3-(benzimidazol-2-yl)thiomethylcephalosporanic acid was charged into a 300-ml three-necked flask, and then dissolved in 100 ml of an aqueous solution of sodium hydrogencarbonate so that the resulting solution had a pH value of 7.0 to 7.5. A solution of 3.0 g of a 1H-1,2,3-triazol-5-ylthiol ester of p-hydroxy-N-formylphenylglycine in 50 ml of dimethylformamide was dropped into the three-necked flask over a period of 15 minutes at room temperature. The pH value of the liquid mixture was adjusted to 4.1 by diluted hydrochloric acid, and the mixture was heated at 60° C. and stirred for 1 hour. The pH value of the reaction mixture was adjusted to 8.0 by sodium hydrogencarbonate to effect deformylation. After completion of the deformylation, the reaction mixture was directly subjected to fractional high-speed liquid chromatography to obtain a fraction of the intended product. The fraction was concentrated under reduced pressure and freeze-dried to obtain 4.3 g of 7-(p-hydroxyphenylglycinamido)-7-methoxy-3-(1H-triazol-5-yl)thiomethylcephalosporanic acid in the form of a white solid (the yield was 85%). The product had a purity of 93%.

Conditions for the fractional high-speed liquid chromatography were the same as those adopted in Example 22.

EXAMPLE 24

Substantially the same procedures in Example 23 were repeated except that a compound shown in Table 6 was used instead of the 1H-1,2,3-triazol-5-ylthiol ester of p-hydroxy-N-formylphenylglycine. The obtained results are shown in Table 6.

TABLE 6

| Run | Starting Compound Kind | Amount (g) | Product Kind | Amount (g) | Yield (%) | Purity (%) |
|---|---|---|---|---|---|---|
| a | 2-methyl-1,3,4-thiadiazol-5-ylthio ester of p-hydroxy-N—formylphenylglycine | 3.3 | 7-(p-hydroxyphenylglycylamido)-7-methoxy-3-(2-methyl-1,3,4-thiadiazol-5-yl)thiomethylcephalosporanic acid | 4.6 | 87 | 95 |
| b | 1-methyl-1,2,3,4-tetrazol-5-ylthio ester of p-hydroxy-N—formylphenylglycine | 3.2 | 7-(p-hydroxyphenylglycylamido)-7-methoxy-3-(1-methyl-1,2,3,4-tetrazol-5-yl)-thiomethylcephalosporanic acid | 4.3 | 83 | 92 |

EXAMPLE 25

3.9 g of 7-methoxy-7-amino-3-(benzimidazol-2-yl)thiomethylcephalosporanic acid was charged into a 300-ml three-necked flask was charged with, and then dissolved in 100 ml of an aqueous solution of sodium hydrogencarbonate so that the resulting solution had a pH value of 7.0 to 7.5. A solution of 4.0 g of a 1H-1,2,3-triazol-5-ylthio ester of N-carbobenzyloxy-p-hydroxyphenylglycine in 50 ml of dimethylformamide was dropped into the three-necked flask over a period of 15 minutes at room temperature. The pH value of the resulting mixture was adjusted to 4.1 by diluted hydrochloric acid, and the mixture was heated at 60° C. and stirred for 15. hours. After completion of the reaction, the pH value of the reaction mixture was adjusted to 2.0 by hydrochloric acid and then the reaction mixture was extracted with ethyl acetate. The ethyl acetate was removed from the extract by distillation under reduced pressure, and the residue was dissolved in an aqueous solution of hydrobromic acid and the solution was stirred at room temperature for 5 hours. After completion of the reaction, the reaction mixture was subjected to fractional high-speed liquid chromatography to obtain a fraction of the intended product. The fraction was concentrated under reduced pressure and freeze-dried to obtain 4.2 g of 7-(p-hydroxyphenylglycinamido)-7-methoxy-3-(1H-1,2,3-triazol-5-yl)thiomethylcephalosporanic acid in the form of a white solid (the yield was 85%). The product had a purity of 93%.

Conditions for Fractional High-Speed Liquid Chromatography

Chromatograph: System Model 500 supplied by Waters Assoc. Co.
Solvent: methanol/water (40/60 by volume)
Column: fractional column, Prep-PAK C18
Flow rate: 100 ml/min

EXAMPLE 26

A 2-liter three-necked flask equipped with a thermometer was charged with 18.1 g of 7-amino-3-(benzimidazol-2-yl)thiomethyl-3-cephem-4-carboxylic acid, 300 ml of N,N-dimethylformamide and 700 ml of water, and the mixture was heated at 60° C. and stirred. Then, 15.5 g of a 1-methyltetrazol-5-ylthio ester of trifluoromethylthioacetic acid was added to the mixture, and 20 ml of 0.5 N aqueous hydrochloric acid was further added as a reaction catalyst. The mixture was stirred at 60° C. for 2 hours to complete the reaction. When the reaction mixture was determined by high-speed liquid chromatography, it was found that the conversion was 84%. The reaction mixture was cooled and impurities were removed from the reaction mixture by extraction with ether according to customary procedures. Then, the pH value of the reaction mixture was reduced to 1.5 by 1 N aqueous hydrochloric acid and the reaction product was extracted with 1 liter of ethyl acetate three times. The extract was dried over anhydrous magnesium sulfate and the solvent was removed by distillation under reduced pressure to obtain 15.8 g of 7-(trifluoromethylthioacetoamido)-3-(1-methyltetrazol-5-yl)thiomethyl-3-cephem-4-carboxylic acid (Cefazaflur) in the form of a white powder. The product had a purity of 98%.

| | Elementary Analysis | |
| --- | --- | --- |
| | Calculated | Found |
| C | 33.2% | 33.1% |
| N | 17.9% | 17.8% |
| F | 12.1% | 12.1% |
| S | 20.4% | 20.5% |
| H | 2.8% | 2.8% |

EXAMPLE 27

A 3-liter three-necked flask equipped with a thermometer was charged with 27.2 g of 7-aminocephalosporanic acid, 600 ml of acetone and 1400 ml of water, and the mixture was heated at 60° C. and stirred. Then, 31.0 g of a 1-methyltetrazol-5-ylthio ester of trifluoromethylthioacetic acid was added to the solution, and the resulting mixture was stirred at 60° C. for 5 hours to complete the reaction. When the reaction mixture was determined by high-speed liquid chromatography, it was found that the conversion was 58%. The reaction mixture was cooled and impurities were removed from the reaction mixture by extraction with ether according to customary procedures. The pH value of the reaction mixture was reduced to 1.5 by 1 N aqueous hydrochloric acid, and the reaction product was extracted with 2 liters of ethyl acetate three times. The extract was dried over anhydrous magnesium sulfate and the solvent was removed by distillation under reduced pressure to obtain 23.2 g of 7-(trifluoromethylthioacetamido)-3-(1-methyltetrazol-5-yl)thiomethyl-3-cephem-4-carboxylic acid in the form of a white powder. The product had a purity of 97%.

EXAMPLE 28

A 3-liter three-necked flask equipped with a thermometer was charged with 36.2 g of 7-amino-3-(benzimidazol-2-yl)thiomethyl-3-cephem-4-carboxylic acid, 600 ml of N,N-dimethylformamide and 1400 ml of water, and the mixture was heated at 60° C. and stirred. Then, 27.5 g of a 1-methyltetrazol-5-ylthio ester of cyanomethylthioacetic acid was added to the mixture, and 40 ml of 0.5 N aqueous hydrochloric acid was further added as a reaction catalyst. The mixture was stirred at 60° C. for 1.5 hours to complete the reaction. When the reaction mixture was determined by high-speed liquid chromatography, it was found that the conversion was 83%. The reaction mixture was cooled, and impurities were removed from the reaction mixture by extraction with ether according to customary procedures. The pH values of the reaction mixture was reduced to 1.5 by 1 N aqueous hydrochloric acid, and the reaction product was extracted with 2 liters of ethyl acetate three times. The extract was dried over anhydrous magnesium sulfate and the solvent was removed by distillation under reduced pressure to obtain 28.6 g of 7-(cyanomethylthioacetamido)-3-(1-methyltetrazol-5-yl)thiomethyl-3-cephem-4-carboxylic acid in the form of a white powder. The product had a purity of 97%.

| | Elementary Analysis | |
| --- | --- | --- |
| | Calculated | Found |
| C | 38.1% | 38.1% |
| N | 22.2% | 22.1% |
| S | 21.8% | 21.9% |
| H | 3.4% | 3.3% |

EXAMPLE 29

A 300-ml three-necked flask equipped with a thermometer was charged with 2.72 g of 7-aminocephalosporanic acid, 60 ml of acetone and 140 ml of water, and the mixture was heated at 60° C. and stirred. Then, 2.75 g of a 1-methyltetrazol-5-ylthio ester of cyanomethylthioacetic acid was added to the mixture, and the resulting mixture was stirred at 60° C. for 6 hours to complete the reaction. When the liquid reaction mixture was determined by high-speed liquid chromatography, it was found that the conversion was 52%. The reaction mixture was cooled and impurities were removed from the reaction mixture by extraction with ether according to customary procedures. Then, the pH value of the reaction mixture was reduced to 1.5 by 1 N aqueous hydrochloric acid and the reaction product was extracted with 200 ml of ethyl acetate three times. The extract was dried over anhydrous magnesium sulfate and the solvent was removed by distillation under reduced pressure to obtain 1.83 g of 7-(cyanomethylthioacetamido)-3-(1-methyltetrazol-5-yl)thiomethyl-3-cephem-4-carboxylic acid in the form of a white powder. The product had a purity of 98%.

EXAMPLE 30

A 2-liter three-necked flask equipped with a thermometer was charged with 18.1 g of 7-amino-3-(benzimidazol-2-yl)thiomethyl-3-cephem-4-carboxylic acid, 300 ml of N,N-dimethylformamide and 700 ml of water, and the mixture was heated at 60° C. and stirred. Then, 14.4 g of a 1-methyltetrazol-5-ylthio ester of 2-thienylacetic acid was added to the mixture, and 20 ml of 0.5 N aqueous hydrochloric acid was further added as a reaction catalyst. The mixture was stirred at 60° C. for 2 hours to complete the reaction. When the reaction mixture was determined by high-speed liquid chromatography, it was found that the conversion was 81%. The liquid reaction mixture was cooled and impurities were removed from the reaction mixture by extraction with ether according to customary procedures. Then, the pH value of the reaction mixture was reduced to 1.5 by 1 N aqueous hydrochloric acid and the reaction product was extracted with 1 liter of ethyl acetate three times. The extract was dried over anhydrous magnesium sulfate and the solvent was removed by distillation under reduced pressure to obtain 13.7 g of 7-(2-thienylacetamido)-3-(1-methyltetrazol-B 5-yl)thiomethyl-3-cephem-4-carboxylic acid in the form of a white powder. The product had a purity of 96%.

| | Elementary Analysis | |
|---|---|---|
| | Calculated | Found |
| C | 42.5% | 42.4% |
| N | 18.6% | 18.6% |
| S | 21.2% | 21.3% |
| H | 3.5% | 3.4% |

EXAMPLE 31

A 3-liter three-necked flask equipped with a thermometer was charged with 27.2 g of 7-aminocephalosporanic acid, 500 ml of acetone and 1500 ml of water, and the mixture was heated at 60° C. and stirred. Then, 23.3 g of a 1-methyltetrazol-5-ylthio ester of 2-chloroacetic acid was added to the mixture. The resulting mixture was stirred for 60° C. for 6 hours to complete the reaction. When the reaction mixture was determined by high-speed liquid chromatography, it was found that the conversion was 53%. The reaction mixture was cooled and impurities were removed from the reaction mixture by extraction with ether according to customary procedures. The pH value of the reaction mixture was reduced to 1.5 by 1 N aqueous hydrochloric acid and the reaction product was extracted with 2 liters of ethyl acetate three times. The extract was dried over anhydrous magnesium sulfate and the solvent was removed by distillation under reduced pressure to obtain 15.3 g of 7-(2-chloroacetamido)-3-(1-methyltetrazol-5-yl)thiomethyl-3-cephem-4-carboxylic acid in the form of a white powder. The product had a purity of 97%.

EXAMPLE 32

A 2-liter three-necked flask equipped with a thermometer was charged with 19.6 g of 7-amino-7-methoxy-3-(benzimidazol-2-yl)thiomethylcephalosporanic acid, 300 ml of N,N-dimethylformamide and 700 ml of water, and the mixture was heated at 60° C. and stirred. Then, 15.5 g of a 1-methyltetrazol-5-ylthio ester of trifluoromethylthioacetic acid was added to the mixture and 20 ml of 0.5 N aqueous hydrochloric acid was further added as a reaction catalyst. The resulting mixture was stirred at 60° C. for 90 minutes to complete the reaction. When the reaction mixture was determined by high-speed liquid chromatography, it was found that the conversion was 93%. The reaction mixture was cooled and impurities were removed from the reaction mixture by extraction with ether according to customary procedures. Then, the pH value of the reaction mixture was adjusted to 1.5 by 1 N aqueous hydrochloric acid and the reaction product was extracted with 1 liter of ethyl acetate three times. The extract was washed with water and dried over anhydrous magnesium sulfate, and the solvent was removed by distillation under reduced pressure to obtain 17.5 g of 7-(trifluoromethylacetamido)-7-methoxy-3-(1-methyltetrazol-5-yl)thiomethylcephalosporanic acid in the form of a light yellow powder. The product had a purity of 93%.

EXAMPLE 33

A 3-liter three-necked flask equipped with a thermometer was charged with 30.2 g of 7-amino-7-methoxycephalosporanic acid, 600 ml of acetone and 1400 ml of water, and the mixture was heated at 60° C. and stirred. Then, 15 g of a 1-methyltetrazol-5-ylthio ester of 2-chloroacetic acid was added to the mixture. The resulting mixture was stirred at 50° C. for 6 hours to complete the reaction. When the reaction mixture was determined by high-speed liquid chromatography, it was found that the conversion was 56%. The reaction mixture was cooled and impurities were removed from the reaction mixture by extraction with ether according to customary procedures. Then, the pH value of the reaction mixture was adjusted to 1.5 by 1 N aqueous hydrochloric acid and the reaction product was extracted with 2 liters of ethyl acetate three times. The extract was washed with water and dried over anhydrous magnesium sulfate, and the solvent was removed by distillation under reduced pressure to obtain 17.0 g of 7-(2-chloroacetamido)-7-methoxy-3-(1-methyltetrazol-5-yl)thiomethylcephalosporanic acid in the form of a light yellow powder. The product had a purity of 95%.

EXAMPLE 34

Substantially the same procedures as in Example 32 were repeated except that 17.2 g of a 1-methyltetrazol-5-ylthio ester of cyanomethylthioacetic acid was used instead of the 1-methyltetrazol-5-ylthio ester of trifluoromethylthioacetic acid, to obtain 16.5 g of 7-(cyanomethylthio)acetamido-7-methoxy-3-(1-methyltetrazol-5-yl)thiomethylcephalosporanic acid (Ceftezole) in the form of a light yellow powder. The product had a purity of 93%.

EXAMPLE 35

Substantially the same procedures as in Example 33 were repeated except that 36 g of a 1-methyltetrazol-5-ylthio ester of 2-thienylacetic acid was used instead of the 1-methyltetrazol-5-ylthio ester of 2-chloroacetic acid, to obtain 18.9 g of 7-(2-thienyl)acetamido-7-methoxy-3-(1-methyltetrazol-5-yl)thiomethylcephalosporanic acid in the form of a light yellow powder. The product had a purity of 88%.

EXAMPLE 36

A 3-liter three-necked flask equipped with a thermometer was charged with 27.9 g of 7-amino-7-methoxy-3-chloromethylcephalosporanic acid, 600 ml of acetone and 1400 ml of water, and the mixture was heated at 60° C. and stirred. Then, 36 g of a 1-methyltetrazol-5-ylthio ester of 2-thienylacetic acid was added to the mixture, and the resulting mixture was stirred at 50° C. for 6 hours while controlling the pH value at 6.5. After completion of the reaction, the reaction mixture was determined by high-speed liquid chromatography. It was found that the conversion was 45%. The reaction mixture was cooled and impurities were removed from the reaction mixture by extraction with ether according to customary procedures. The pH value of the reaction mixture was adjusted to 1.5 by 1 N aqueous hydrochloric acid, and the reaction product was extracted with 2 liters of ethyl acetate three times. The extract was washed with water and dried over anhydrous magnesium sulfate and the solvent was removed by distillation under reduced pressure to obtain 20.6 g of 7-(2-thienyl)acetamido-7-methoxy-3-(1-methyltetrazol-5-yl)thiomethylcephalosporanic acid in the form of a yellow solid. The product had a purity of 79%.

What is claimed is:

1. A thioester compound represented by the following general formula (I):

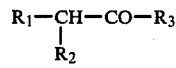

wherein $R_1$ represents a cyanomethylthio group, wherein $R_2$ represents a hydrogen atom and wherein $R_3$ represents a 1-methyl-1,2,3,4-tetrazol-5-ylthio group.

* * * * *